United States Patent
Pologe

(10) Patent No.: US 10,863,937 B2
(45) Date of Patent: Dec. 15, 2020

(54) EX VIVO CALIBRATION OF A PHOTOPLETHYSMOGRAPHIC DEVICE

(71) Applicant: Jonas Alexander Pologe, Boulder, CO (US)

(72) Inventor: Jonas Alexander Pologe, Boulder, CO (US)

(73) Assignee: Kestrel Labs, Inc, Boulder, CO (US)

( * ) Notice: Subject to any disclaimer, the term of this patent is extended or adjusted under 35 U.S.C. 154(b) by 324 days.

(21) Appl. No.: 15/903,939

(22) Filed: Feb. 23, 2018

(65) Prior Publication Data

US 2019/0261901 A1 Aug. 29, 2019

(51) Int. Cl.
| | |
|---|---|
| *A61B 5/1495* | (2006.01) |
| *G01N 33/49* | (2006.01) |
| *A61B 5/024* | (2006.01) |
| *A61B 5/1455* | (2006.01) |

(52) U.S. Cl.
CPC ........ *A61B 5/1495* (2013.01); *A61B 5/02416* (2013.01); *G01N 33/4925* (2013.01); *A61B 5/14551* (2013.01); *A61B 2560/0223* (2013.01)

(58) Field of Classification Search
None
See application file for complete search history.

(56) References Cited

U.S. PATENT DOCUMENTS

| 5,278,627 A | 1/1994 | Aoyagi | |
|---|---|---|---|
| 5,891,025 A | 4/1999 | Buschmann | |
| 2010/0160751 A1* | 6/2010 | Hete | A61B 5/14557 600/322 |
| 2011/0120206 A1* | 5/2011 | Troughton | A61B 5/1495 73/1.06 |
| 2013/0172803 A1* | 7/2013 | Olde | A61M 1/3653 604/6.11 |
| 2015/0208923 A1* | 7/2015 | Akl | A61B 5/0084 600/479 |

* cited by examiner

*Primary Examiner* — Etsub D Berhanu
*Assistant Examiner* — Aurelie H Tu

(57) ABSTRACT

A method for calibration of a photoplethysmographic device including the steps of providing a fluid circuit (305) for blood or other liquid, a pump mechanism (310) to generate pulsatile flow of blood through the fluid circuit, a sample of excised tissue (315) in the fluid circuit through which the blood flows, and a photoplethysmographic device including an emitter and a photodetector (330) positioned on the tissue (335, 340) so that a portion of the light output by the emitter passes through the tissue and is incident on the photodetector. The method further includes the steps of energizing the pump mechanism (420) to move the blood through the tissue, energizing the emitter (425) to output light, collecting paired data from the photodetector and from one or more reference measurements (430), and processing the paired data to calibrate the photoplethysmographic device (435).

6 Claims, 3 Drawing Sheets

EX VIVO CALIBRATION OF A PHOTOPLETHYSMOGRAPHIC DEVICE

TITLE OF THE INVENTION

Ex Vivo Calibration of a Photoplethysmographic Device

BACKGROUND OF INVENTION

This invention is in the field of noninvasive medical monitoring and more specifically in photoplethysmographic monitoring. This invention provides a method for accurate calibration of a photoplethysmographic device with physiologically representative photoplethysmographic signals but without the need for live subjects.

In the science of photoplethysmography light is used to illuminate, or trans-illuminate, living tissue for the purpose of providing noninvasive measurements of blood analytes or other hemodynamic parameters or tissue properties. In this monitoring modality light is directed into living tissue and a portion of the light which is not absorbed by the tissues, or scattered in some other direction, is detected by a photodetector a short distance from the point at which the light entered the tissue. The detected light is converted, by the photodetector, into an electronic signal that is indicative of the received light intensity exiting the tissue.

The light signal exiting the tissue at the location of the photodetector, assuming that the tissue is perfused with blood from a beating heart, is modulated by the varying blood volume in the tissue that the light passes through on its way from the light source, or sources, to the photodetector. The output light signal received by the photodetector is therefore not constant but decreases and increases in intensity as the blood volume that the light passes through increases and decreases with each heartbeat. This time varying signal originating from one or more light sources, or light channels, is referred to as a photoplethysmographic signal or photoplethysmographic data.

These photoplethysmographic data from the various light sources are used to calculate various blood analyte levels such as arterial blood oxygen saturation and/or hemodynamic variables such as heart rate, cardiac output, or tissue perfusion.

A device which detects and processes photoplethysmographic signals to measure the levels of one or more blood analytes and/or the levels of one or more hemodynamic parameters is referred to as a photoplethysmographic measurement apparatus, photoplethysmographic device, or photoplethysmographic instrument.

The first widespread commercially-used photoplethysmographic device in medicine was the pulse oximeter, a photoplethysmographic device designed to measure arterial blood oxygen saturation and, typically, also the heart rate. In early pulse oximetry, the emitter was a single tungsten light source which output broadband light with optical interference filters applied to the received (detected) light to isolate two narrow spectral bands of light. In current pulse oximetry the emitter typically consists of two discrete light emitting diodes (LEDs) which generate two different bands of light, with each light band possessing a unique spectral content. More recently photoplethysmographic instruments have been developed in which the emitter outputs several discrete light bands, either from a set of LEDs or a set of lasers, or a combination of the two, to allow the measurement of a larger number of blood analytes and/or hemodynamic parameters including such blood analytes as the levels of oxyhemoglobin, carboxyhemoglobin, methemoglobin, and reduced hemoglobin in the arterial blood and such hemodynamic parameters as heart rate, tissue perfusion, respiratory rate, cardiac output, and circulating blood volume, to name just a few.

But photoplethysmographic devices have a somewhat unique problem in the field of medical monitoring that has existed at least since the early days of pulse oximetry in the late 1970s. For the blood analytes and hemodynamic parameters that they measure, calibration—determining the mathematical relationship between the photoplethysmographic data and the desired analyte levels and/or hemodynamic values—is performed on volunteer human subjects and therefore can only be performed over a very limited measurement range.

For a pulse oximeter that measures oxygen saturation, for example, paired data points—photoplethysmographic data from the photodetector paired with reference, or gold standard, oxygen saturation measurements—must be collected in a desaturation study. In this study, human volunteers are used. A catheter is placed in an artery for arterial blood sampling and then the volunteers are systematically, stepwise, desaturated (or reduced in arterial oxygen saturation). At a number of oxygen saturation levels, typically over a range of about 100% down to 70%, photoplethysmographic data is collected and paired with reference measurements of oxygen saturation readings from aliquots of blood sampled from the arterial catheter and measured on a reference laboratory CO-oximeter.

This calibration procedure is both invasive and potentially dangerous and therefore is very limited in the range over which calibration can be performed. As a consequence, no pulse oximeter on the market today is actually calibrated over more than about 35% of the total measurement range for oxygen saturation even though, clinically, a patient can drop well below the calibrated range of the instrument. This problem has been recognized since the commercial introduction of the first pulse oximeter more than 35 years ago, as evidenced, in part, by the numerous attempts to develop alternative calibration methodologies that do not require the use of living subjects.

This problem is further amplified when the photoplethysmographic device is designed to measure a blood analyte such as the carboxyhemoglobin level. In this case the calibration study would require poisoning the subjects with carbon monoxide (to generate the increased carboxyhemoglobin levels). Because this is so dangerous current pulse oximeters, that can also read carboxyhemoglobin levels, are only calibrated for carboxyhemoglobin over a very small range of about 0% to 20%, considerably less than the full clinical range for this parameter.

Several different attempts at in vitro methods were published in Design of Pulse Oximeters (Edited by J. G. Webster, Institute of Physics Publishing, 1997, pp159-173). The methods revealed in this text included numerous blood-based, and non-blood-based, tissue simulators on which a photoplethysmographic sensor could be placed. Various additional attempts at calibration methodologies or apparatuses are revealed in the patent literature. U.S. Pat. No. 5,278,627 reveals a non-blood tissue model apparatus for calibrating a pulse oximeter that pulsates a light absorber, which is intended to absorb light in a manner similar to pulsating blood and which, when placed in a sensor, will generate a photoplethysmographic signal. U.S. Pat. No. 5,891,025 reveals a calibration method and apparatus that uses a blood-based measurement cell with mechanically-imposed pulsation.

All of these simulators and calibration methodologies were designed to generate a pulsatile, or photoplethysmographic, signal that could be used for the purpose of calibration. While each of these attempts appears to be able to generate photoplethysmographic data, none of these methods have provided results that accurately duplicate the calibration for arterial oxygenation that is obtained on living human subjects closely enough to eliminate the need for in vivo human subject testing. It appears that the optical properties of blood in tissue are not adequately replicated by either non-blood tissue models or by blood based tissue simulators. Non-blood simulators have several problems including that the material used to represent the blood does not have the same optical extinction (as a function of wavelength) as human blood making it very difficult to determine what oxygen saturation the measured photoplethysmographic data should be correlated with.

Blood-based tissue simulators have been shown empirically to provide calibration curves that do not match those obtained on living tissue. The cause for this difference appears to be due, in part, to the optical differences in using bulk blood in the measurement cell, upon which the photoplethysmographic sensor is place, as opposed to the having the blood distributed throughout the tissue-under-test in a fine microvascular network such as is found in the microvasculature of the human fingertip.

BRIEF SUMMARY OF THE INVENTION

This patent discloses a method for safe and accurate ex vivo calibration of a photoplethysmographic device that can be performed over the entire clinically-viable measurement range for the analytes and parameters of interest, without the need for living human or animal subjects.

There is a basic problem in the field of photoplethysmography that has existed since its introduction. No commercial photoplethysmographic device has ever been calibrated over the full clinically possible-measurement range, and calibration of these devices typically requires the use of human volunteers and invasive testing. For example the conventional pulse oximeter, the most commonly known photoplethysmographic device, is typically designed to measure arterial blood oxygen saturation over a range from nearly zero to 100%, but these devices are only calibrated over a small fraction of that range, usually from about 70 to 100%.

Calibration of a photoplethysmographic device is defined as generating the relationship between the optical signals received by the photodetector(s) of the photoplethysmographic device (the photoplethysmographic data) and a reference hemodynamic parameter level and/or a reference blood analyte level of interest.

The method of this invention utilizes animal, or human, tissue and blood in combination with an in vitro circulation system designed to perfuse the tissue with the blood and to control the levels of various hemodynamic parameters and/or blood analytes that the photoplethysmographic device is capable of measuring. Hemodynamic parameters that can be measured by photoplethysmography include such parameters as heart rate, circulating blood volume, perfusion index, and respiratory rate. Numerous blood analytes can also be measured by photoplethysmography including arterial oxygen saturation, and the percentages (or even absolute concentrations) of oxyhemoglobin, carboxyhemoglobin, methemoglobin, and reduced hemoglobin in the arterial blood.

By setting, and measuring, specific blood analyte and/or hemodynamic parameter levels, data can be collected both from the photoplethysmographic device and from the measured reference levels and these data can be used to calibrate the device. Current pulse oximeters typically measure at least one blood analyte, oxygen saturation, and the hemodynamic parameters heart rate and perfusion index.

The calibration method of this invention provides at least several crucial advantages over in vivo calibrations performed on live human volunteers. Using excised tissue in combination with a photoplethysmographic device provides the identical optical system seen in clinical or veterinary use of the photoplethysmographic device, and mechanically perfusing this tissue with blood, controlled and supplied by an in vitro circulation system, allows precise control of the analyte levels and parameter levels of interest. Further, because the tissue used in this calibration method is ex vivo the analyte and parameter levels can be adjusted to allow calibration over the full clinically-viable measurement range.

The combination of an in vitro circulation system with ex vivo tissue to create the ex vivo calibration method described in this invention allows, for the first time, accurate calibration of a photoplethysmographic device over the full measurement range of the blood analyte levels and/or the hemodynamic parameter levels of interest, without the need for, or risk of harm to, living human or animal study subjects.

DETAILED DESCRIPTION OF THE INVENTION

Photoplethysmographic devices have been in widespread use for over 30 years. Photoplethysmographic devices illuminate living tissue with specific wavelength bands of light. A portion of the light that is incident on the tissue passes through the tissue and is received a short distance from where it enters the tissue. The received light has been modulated by the blood pulsating through the tissue, causing the received intensity to decrease and increase as the blood volume in the tissue-under-test increases and decreases with the pulsatile blood flow. It is this pulsatile light signal (also referred to as a photoplethysmographic signal or the photoplethysmographic data) that the photoplethysmographic device processes to provide the measurements of interest such as arterial blood oxygenation and heart rate.

By using excised tissue in combination with an artificial circulation system, accurate calibration of a photoplethysmographic device can be performed without the need for human volunteers (or the use of laboratory animals), and these calibrations can be made over the full clinically-viable range of the hemodynamic parameter levels and/or blood analyte levels of interest.

Figure 1:
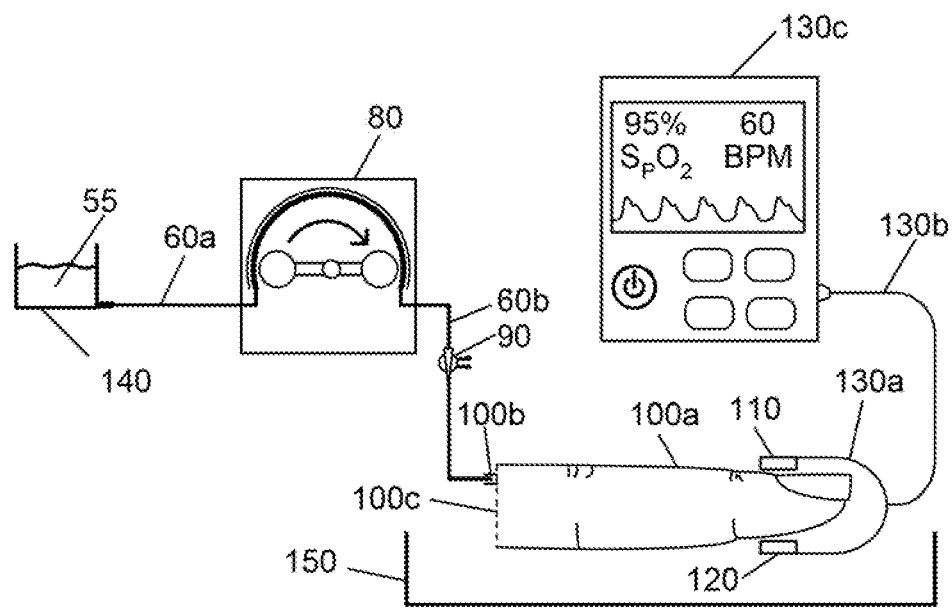
FIG. 1. Minimal configuration for ex vivo calibration.

FIG. 1 shows one possible basic set up for the in vitro calibration method of this invention. Blood 55, obtained from the species to be tested (e.g. human blood obtained from a blood bank), is provided in container 140. Preferably this blood would be as fresh as possible to be as optically identical as possible to blood in living tissue. The blood would also typically be prevented from coagulating before use. This can be accomplished in any of a number of different ways including the addition of an anticoagulant such as heparin or by centripetal separation of the blood, disposal of the plasma portion, and rehydration of the red blood cells with normal saline solution.

This blood is introduced into a fluid circuit (60a and 60b) being drawn into fluid circuit portion 60a by a pump mechanism 80 which is incorporated in the fluid circuit to move blood 55 from the container 140 towards a tissue sample 100a, 100b, and 100c (also referred to as the tissue-under-test or, simply, the tissue). The output fluid flow from the pump mechanism 80, typically the movement of blood through the fluid circuit, in FIG. 1 continues on through the next section of the fluid circuit, 60b, in the direction of the tissue 100a, 100b, and 100c. The fluid circuit, 60a and 60b, can be tubing, or any other mechanism that constrains the blood flow to and from the pump. For example 60a and 60b could consist of actual blood vessels, or 60a and/or 60b could be a physical part of the pump mechanism 80.

The pump mechanism 80 is specifically designed, or selected, to generate pulsatile fluid flow. Thus the pump mechanism 80 could consist of a common peristaltic pump as indicated in FIG. 1 where flexible tubing is situated against a semicircular wall and rollers move along the tubing compressing it and causing positive displacement of the fluid in the tubing in the direction that the rollers move. As the rollers come off the tubing, at the end of semicircular wall, the compression of the tubing is released and the flow momentarily slows down, thus the fluid flow is pulsatile in nature.

There are also many other options for configuring a pump mechanism that generates pulsatile fluid flow. For example, a syringe pump could be driven by a computer controlled stepper motor programmed to provide pulsatile flow with essentially any desired flow profile. And the flow profile could be programmed to change dynamically over time thereby varying the flow rate, flow amplitude, pulse frequency, and/or pulse profile. Alternatively the pump mechanism could consist of a constant velocity pump (a non-positive displacement pump) followed by a short stretch of flexible tubing that could be rhythmically compressed and released by a small paddle to generate pulsatile flow in the output side of the tubing. By programming the movement of the paddle, the output fluid flow (or blood flow) could again be caused to vary in flow rate, pulse rate, pulse shape, and pulse amplitude as desired.

The tissue 100a, 100b, and 100c is excised tissue, typically selected to be the type of tissue that a photoplethysmographic device would commonly be used on. For example it could be a finger or an ear of a recently deceased animal or human. Preferably one would select the tissue to be from the specific species on which one would like to calibrate the photoplethysmographic device. Further the tissue should be as intact as possible to ensure that the optical system that the photoplethysmographic device "sees" while making readings on the tissue matches that which would be obtained on living tissue of the same type and species.

The tissue 100a including at least one artery 100b and one venous return portion 100c is integrated into the fluid circuit to receive the fluid flow output by the pump mechanism 80. The fluid flow from fluid circuit portion 60b is connected to at least one artery 100b in the tissue 100a to supply blood to the tissue 100a. Connection from the fluid circuit portion 60b to the artery 100a can be accomplished by catheterizing the artery 100a with a short length of tubing and then gently tying a loop around the artery and the tubing to effectively seal the artery to the tubing.

Fluid exiting the tissue 100a drains from the venous return portion 100c of the tissue. This venous return portion 100c can simply be the proximal end of a finger as indicated in FIG. 1. Blood return from most tissue samples, such as an excised finger, typically does not occur through just a single vein but through a disperse network of veins, thus the venous return portion 100c is simply the portion of the tissue 100a where the blood exits the tissue. In a simplistic embodiment of this invention collection of blood 55 exiting the tissue 100a can be as simple as allowing the blood 55 to exit the tissue 100a at the venous return portion 100c and simply drip out into a collection container 150 or directly into a disposal drain.

A photoplethysmographic device commonly includes a monitor portion 130c, a sensor cable, or patient cable, 130b, and a sensor 130a. But this is only one possible configuration for a photoplethysmographic device. For example, many finger oximeters available on the market today include a monitor and a sensor in a single integrated unit that looks like a finger clip and which typically incorporates a display on the top side of the device. These types of photoplethysmographic devices eliminate the need for a patient cable altogether. Another configuration separates the sensor portion from the display or monitor portion but does not use a physical cable to connect the sensor portion to the monitor portion but instead uses radio frequency communication to connect the output of the sensor with the monitor portion. Still another configuration of photoplethysmographic device uses a smart phone as the display portion of the device and the sensor and associated electronics output data directly to the smart phone.

Regardless of the exact configuration of the photoplethysmographic device 130a, 130b, and 130c, an emitter 110 and a photodetector 120 must be directed at the tissue 100a to allow a photoplethysmographic signal to be obtained. Most commonly, the tissue 100a is transilluminated by placing the emitter 110 that is energized by the photoplethysmographic device in close proximity to or against the tissue 100a as shown in FIG. 1. The light exiting the emitter 110 is then incident on the tissue 100a. This light then passes through the tissue 100a and some portion of the light that is not otherwise absorbed or scattered in a direction away from the photodetector 120 is received by the photodetector 120 and converted into an electronic signal which is an electrical representation of the photoplethysmographic signal. It is this electronic signal, or photoplethysmographic data, from the photodetector 120 that is processed to determine the various blood analyte levels and hemodynamic parameters that the photoplethysmographic device 130a, 130b, and 130c is designed to read. For example the blood analyte level might be the arterial oxygen saturation and the hemodynamic parameter value might be the pulse rate, as shown on monitor portion 130c in FIG. 1.

The emitter 110 is the portion of the sensor 130a where the sensing light exits the sensor 130a to be incident on the tissue 110. The light output from the emitter can be broadband light, one or more discrete spectral bands of light, or any combination of the two.

It is also well recognized in the field of photoplethysmography that the emitter 110 and the detector 120 can be placed on opposite sides of a tissue-under-test or nearly side-by-side on the tissue-under-test. Because of the scattering of the emitted light by the tissue-under-test (and primarily by the red blood cells in the tissue-under-test) some portion of the light entering the tissue-under-test will by scattered and eventually emitted toward the photodetector regardless of whether it is placed on opposite sides of a tissue-under-test from the emitter, in what is referred to as transmission mode, or side-by-side with the emitter on the tissue-under-test, in what is often referred to as reflectance mode.

To allow sampling of the blood 55 that is passing through the tissue 100a a sample access port 90 can be included in the fluid circuit. In FIG. 1 the sample port is shown in fluid circuit portion 60b. In practice this port 90 could be placed virtually anywhere in the circuit, as long as the blood 55 at that point in the circuit has the same analyte levels as the blood 55 that passes through the tissue 100a.

Figure 2:
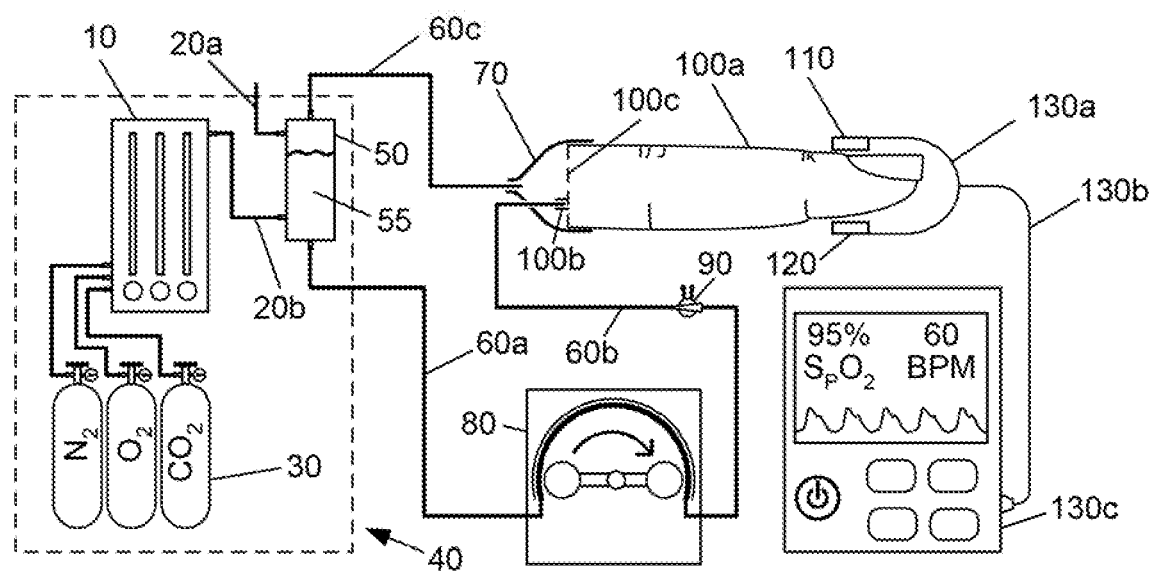
FIG. 2. Detailed configuration for ex vivo calibration.

FIG. 2 illustrates an alternate configuration, of a portion of the invention, using a substantially enclosed fluid circuit. In this configuration many of the same elements exist as in FIG. 1 but the containers 140 and 150 have been eliminated and a circular circuit has been created where the same volume of blood 55 is run through the tissue 100a repeatedly.

In this configuration the blood 55 passes through a tonometer 50. The tonometer 50 can be used to control various blood analyte levels such as the oxygen saturation level, the oxyhemoglobin level, the carboxyhemoglobin level, and the methemoglobin level. The tonometer 50 in combination with a number of other elements, indicated by dashed line 40, is designed to provide a means of controlling the partial pressures of various gasses in the blood 55 thereby controlling the levels of certain blood analytes. For example to control the oxyhemoglobin level in the blood three gas supplies 30 (e.g. oxygen, nitrogen, and carbon dioxide) could be connected to a multi gas mixer 10. By selecting the right proportion of each of these gasses with the multi gas mixer 10—flowing from the mixer 10, through gas supply line 20b, to the tonometer, and eventually out the vent line 20a—the oxyhemoglobin of the blood 50 could be set to almost any desired level. Similarly, if it was desirable to control the carboxyhemoglobin level, a carbon monoxide gas supply could be added to the mix to supply controlled levels of carbon monoxide to the tonometer 50.

One type of tonometry system commonly used in medical practice is an extra corporeal membrane oxygenator or ECMO system. ECMO systems are used to properly oxygenate the blood of a patient who, for whatever reason, is not able to maintain an acceptable oxygen saturation level on their own.

By creating a substantially enclosed fluid circuit it is easier to control and maintain a given set of blood analyte levels. For example to maintain a stable, fixed, and low oxyhemoglobin level requires preventing the blood 55 from being exposed to the atmosphere where it would pick up additional oxygen and rise in saturation level.

Also, in the configuration shown in FIG. 2, the venous return portion 100c is captured by an enclosure 70 to allow the blood 55 exiting the venous return portion 100c to be returned to the tonometer 50 through fluid circuit portion 60c. The enclosure 70 further prevents the blood 55 from being exposed to ambient air and connects the venous return portion of the tissue-under-test, 100a, to the fluid circuit portion 60c. The enclosure 70 can be constructed of a silicone rubber, or similar material, funnel that fits snugly over the venous return portion 100c and seals on the other end to fluid circuit portion 60c (allowing a pass-through, ideally air tight, for connection to the artery 100b). Note that fluid circuit portion 60c could again be a length of tubing or it could simply be the connection to the tonometer 50. Thus FIG. 2 shows a enclosed fluid circuit where the blood in the circuit has little, or no, direct exposure to the ambient air.

As in FIG. 1, the sample access port 90 shown in FIG. 2 can be positioned at any point in fluid circuit 60a, 60b, or 60c, as long as the blood analyte levels sampled at that point in the circuit matches the blood analyte levels of the blood 55 in the tissue 100a.

FIG. 1 and FIG. 2 point to the blood 55 in the container 140 or the tonometer 50, however, when photoplethysmographic data is being collected from the photodetector the pump mechanism 80 is energized and the blood 55 is flowing throughout the fluid circuit, including all elements included or incorporated in the circuit for the given set up. For example, if the configuration shown in FIG. 1 is in use then the blood is flowing through at least the fluid circuit portions 60a, 60b, the tissue 100a, 100b and 100c, and the pump 80 while traveling from container 140 to collection container 150.

Figure 3:
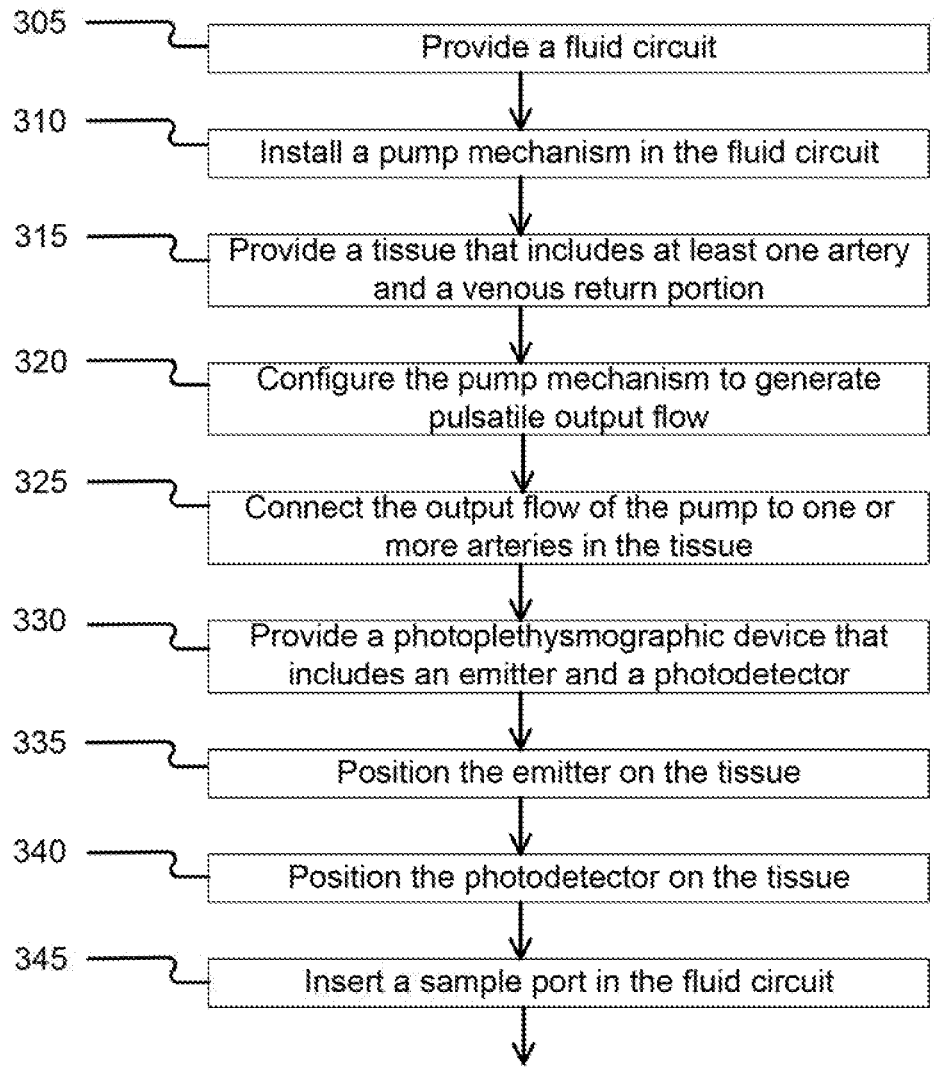
FIG. 3. Detailed calibration flow chart.
Figure 4:
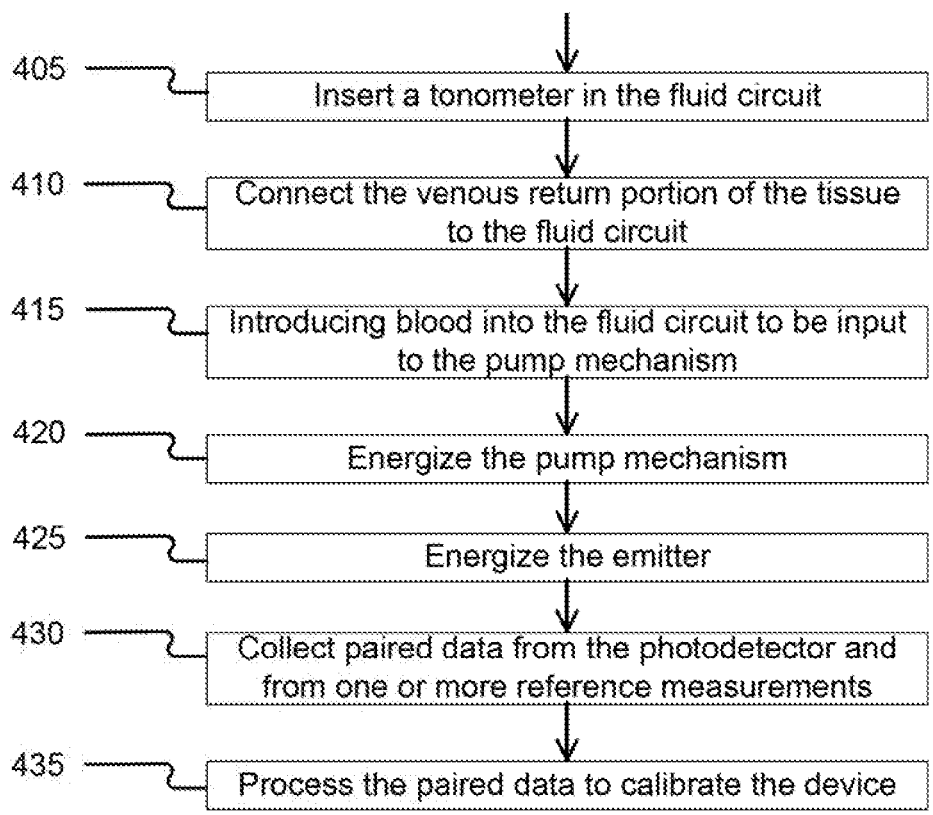
FIG. 4. Detailed calibration flow chart, continued.

The above detailed description describes the key physical elements used for the implementation of the method of this invention. FIG. 3 and FIG. 4 provide a flowchart of the method of this invention.

Referring to FIG. 3 the first step 305 is to provide a fluid circuit. The fluid circuit is a path for blood to follow as it moves through the circuit. This path can consist of any combination of flexible tubing, rigid tubing, blood vessels, or even, potentially, just an open channel. The fluid circuit simply has to conduct blood from one part of the circuit to the next. The next step is to install a pump mechanism in the fluid circuit 310. As described earlier, this pump mechanism must be configured to provide pulsatile flow 320 at its output so that, as the blood flows through the circuit, it generates a volumetric pulsation in the tissue which can then create a photoplethysmographic signal.

Excised tissue is also provided 315 for use in the circuit. This tissue must have an intact artery through which it is connected to the fluid circuit 325. This connection could be through a portion of the fluid circuit 60b or it could be directly connected to the output of the pump mechanism 80. In either case the connection from the pump mechanism 80 to the artery 100b must be made through an enclosed conductor 60b, such as a length of tubing, so that the pulsatile flow is transmitted to the tissue 100a creating volumetric pulsation in the tissue 100a which in turn creates a photoplethysmographic signal when light is passed through the tissue 100a.

Another step is to insert a sample port in the fluid circuit 345. It is advantageous for the sample port 90 of the circuit to be inserted between the pump mechanism 80 and the tissue 100a. This allows easy sampling of the blood 55 for invasive reference measurements of blood analytes just before the blood enters the tissue 100a.

The next three steps are to provide a photoplethysmographic device including an emitter and a photodetector 330, and to position the emitter and the photodetector on the tissue (335 and 340). It is not a requirement that the emitter and photodetector be in physical contact with the tissue 100a but this is typically the way that sensing in photoplethysmography is done, as most sensors clip or tape onto the tissue-under-test. It is possible, however, to perform this sensing with the emitter 110 and/or the photodetector 120 not in direct contact with the tissue 100a by simply projecting light at the tissue 100a and receiving the light that exits some portion of the tissue 100a.

If it is desirable to be able to control certain blood analytes, such as oxyhemoglobin, within the circuit, then a tonometer can also be incorporated in the circuit 405. This is not a required step as one could set the blood to the desired level of any number of blood analytes externally to the fluid circuit and then simply insert this preconditioned blood into the fluid circuit to be input to the pump mechanism 415. The advantage of incorporating the tonometer 50 directly into the fluid circuit is the ability to alter the blood analyte levels repeatedly for collecting data at a number of different levels without needing to flush the circuit of all blood and then introduce a new sample of blood into the circuit to achieve each new set of desired analyte levels.

Once blood is flowing through the tissue 100a it will exit this tissue through the venous return portion of the tissue 100c, thus it is necessary to connect the venous return portion of the tissue 100c to the fluid circuit 410. This can be as trivial as allowing the blood to exit the venous return portion of the tissue 100c and to drop into a collection container 150, and this collection container 150 could simply be a drain. Alternatively, connecting the venous return portion of the tissue 100c to the fluid circuit this could entail connecting the output blood flow from the tissue 100a, exiting the venous return portion of the tissue 100c, to a return portion of the fluid circuit 60c. Again, this connection 60c can be through a length of tubing or channeling or it could be a direct connection to another element in the circuit such as the tonometer 50.

Once the circuit is fully configured and assembled as desired the next step is to energize the pump mechanism 420 to start the blood 55 flowing and pulsating through the circuit and to energize the emitter 425 so that it is outputting light and projecting that light into the tissue 100a. Energizing the emitter typically entails powering on the photoplethysmographic device to cause the emitter to project light into the tissue-under-test and also to start receiving photoplethysmographic data from the photodetector 120 for processing by the electronics of the photoplethysmographic device.

The final two steps are to collect paired data from the photodetector 120 and from reference measurements 430 and to process these data to calibrate the photoplethysmographic device 435. These two steps are described in detail below.

Calibration of virtually any instrument typically involves collection of paired data samples, or measurements, from both the instrument to be calibrated and from a gold standard or "reference" instrument at a number of different levels over the desired calibration range. For example, to calibrate a mercury thermometer one could measure the height of the column of mercury at 10 different temperatures across the measurement range of the thermometer and, at each of those temperatures, one could also obtain reference measurements of the exact temperature using a previously calibrated, highly accurate temperature sensor. This calibration study would provide two columns of data with the first column being the measured reference temperatures and the second column being the measured heights. Each row would be the temperature and height data that was collected at a given temperature thus each row would also be a paired data sample. Finally a calibration equation defining the mathematical relationship could be derived for the height as a function of temperature. For this example, assuming that the height of the column of mercury increases linearly with temperature, the mathematical relationship might take the form shown in Equ 1:

$$\text{Height} = (\text{Degree C} * K) + b \quad \text{Equ 1}$$

In this equation the height (perhaps measured in millimeters of mercury) of the mercury column would be equal to the temperature in ° C. times a constant K, plus a fixed offset b. To obtain the calibration constants K and b, one could perform a linear least squares fit to the paired data samples obtained in the calibration study.

Calibrating a photoplethysmographic device follows these same basic methodological steps (although there are almost an endless number of variations on this scheme that could be employed). For example consider the calibration of a conventional two wavelength pulse oximeter for one blood analyte, oxygen saturation, and for one hemodynamic parameter, pulse rate. To calibrate for oxygen saturation the pulse oximeter sensor is applied to a test subject and an arterial catheter is inserted for arterial blood sampling. A mask is placed over the subject's mouth and nose. The gas mixture provided by mask to the subject controls the arterial oxygen saturation by controlling the ratio of oxygen to nitrogen in the inspired gas mixture.

The goal is to stabilize the subject's arterial oxygen saturation at a number of discrete levels from approximately 100% down to about 70%. Each time the oxygen saturation is stabilized at a given level photoplethysmographic data are collected from the photodetector and an arterial blood sample is withdrawn for analysis on a reference laboratory CO-oximeter to provide a reference measurement of the desired analyte level, in this case oxygen saturation. The inspired gas mixture is then changed, the subject's oxygen saturation stabilized at a new level, and the data collection process is repeated to collect another paired data set.

When enough paired data sets have been collected to allow for a statistically acceptable sample size, the mathematical relationship between the photoplethysmographic data and the oxygen saturation can be derived. Typically this relationship equates the reference oxygen saturation to a ratio of the red wavelength signal over the infrared wavelength signal. While there are many different forms of this relationship the data collection required for this calibration work always requires these paired data samples collected at numerous different blood analyte levels. For a pulse oximeter the calibration equation is often expressed as follows:

$$OS(\%) = aR^2 + bR + c \quad \text{Equ 2}$$

Where $$R = \frac{\Delta R}{R} \bigg/ \frac{\Delta IR}{IR} \quad \text{Equ 3}$$

In Equ 2 OS is the oxygen saturation, in percent. R, also known as the "R Value", is the ratio of a change in light intensity in the red wavelength signal divided by the average light intensity of the red wavelength signal (usually over a fairly short time frame) divided by the same ratio for the infrared signal (over the same time frame), as shown in Equ 3. The constants a, b, and c are the calibration coefficients and can be derived by performing a second-order least squares regression on the paired data samples collected during the calibration study.

Finally, to complete the calibration of the photoplethysmographic device, the calibration constants are installed in the photoplethysmographic device so that, provided any given photoplethysmographic signal data, the device will display (or otherwise output) the appropriate associated oxygen saturation level. Today virtually all pulse oximeters are processor based so installing the calibration coefficients is a matter of programming the calibration equation with the derived calibration coefficients into the code that the pulse oximeter uses to convert the measured R values into oxygen saturation levels.

For the purpose of this invention, processing the paired data to calibrate the photoplethysmographic device 435 is to use the paired data, collected in accordance with this method and as previously described, to either derive the calibration equation with its associated coefficients or to compute the calibration coefficients if the form of the calibration equation is already known, and to install the calibration coefficients and/or the calibration equation into the photoplethysmographic device.

In the above example the calibration equation for only a single blood analyte was derived. The same method described herein can be used to calibrate a photoplethysmographic device for essentially any number of blood analytes. For example, if the photoplethysmographic device was designed to read oxyhemoglobin and carboxyhemoglobin then the paired data sets would include photoplethysmographic data for three or more wavelength channels paired with the reference values for oxyhemoglobin and carboxyhemoglobin, acquired at a large number of oxyhemoglobin and carboxyhemoglobin levels. Then, once again, the paired data would be used to either derive the relationship between the photoplethysmographic signals and the two blood analytes, or to solve for the coefficients of a previously determined form of a set of one or more calibration equations.

To calibrate the photoplethysmographic device for one or more hemodynamic parameter levels the only difference in the calibration method described previously is in how the reference measurements are performed. When the parameter (s) of interest is one or more blood analytes, the blood is sampled and the blood analyte(s) is measured on a laboratory blood analyzer such as a laboratory CO-oximeter. One example of such a reference device is the ABL800 FLEX blood gas analyzer from Radiometer (Radiometer America Inc., Brea, Calif.) which invasively measures numerous blood analytes, including pH, partial pressures of carbon dioxide and oxygen, oxygen saturation, total hemoglobin, hematocrit, the fractions of oxyhemoglobin, carboxyhemoglobin, methemoglobin, and reduced hemoglobin, as well as the concentrations of potassium, calcium, sodium, chloride, blood glucose, lactate, creatinine, and bilirubin, many of which can also be measured by photoplethysmographic techniques.

When calibrating to a hemodynamic parameter level the technique used to obtain the reference measurements is dependent upon the specific hemodynamic parameter. For example, to calibrate the hemodynamic parameter of heart rate, the reference measurement could be as simple as setting the pulse rate of the pump. Then the paired data would consist of pump pulse rate setting paired with the photoplethysmographic signals collected at each pulse rate setting. As an example the photoplethysmographic data could be processed to provide, in place of R values, the number of peaks or valleys found in the photoplethysmographic data over a 60 second period to provide the beats per minute.

One advantage of this ex vivo method of calibration of a photoplethysmographic device for the measurement of heart rate is the ability to generate photoplethysmographic waveforms of all physiologically possible shapes. For instance, photoplethysmographic waveforms could be configured to have large or small dicrotic notches or have large or small amounts of "respiratory artifact" (which shows up as baseline variation in the photoplethysmographic signal). Furthermore, a "respiratory artifact" could be set at the respiratory rate of a tachypnic infant or a bradypnic adult.

Another example of a hemodynamic parameter to calibrate to might be blood pressure. In this case an invasive pressure sensor, such as that used clinically for making continuous arterial blood pressure readings in the hospital, inserted into the fluid circuit portion 60b could provide the reference measurements of arterial blood pressure for pairing with samples of the photoplethysmographic signals.

The previous discussion of the invention has been presented for the purposes of illustration and description. The order of the steps of this method as presented in this description, and as stated in the claims, is not intended to be limiting. Further, the description is not intended to limit the invention to the form disclosed herein. Variations and modifications commensurate with the above are considered to be within the scope of the present invention. The embodiment described herein is further intended to explain the best mode presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

The invention claimed is:

1. A method for in vitro calibration of a photoplethysmographic device comprising the steps of:
   a. providing a fluid circuit;
   b. incorporating a pump mechanism in the fluid circuit;
   c. providing an excised tissue that includes at least one artery and a venous return portion;
   d. configuring the pump mechanism to generate pulsatile output fluid flow through the fluid circuit;
   e. connecting the pulsatile output fluid flow to the at least one artery of the excised tissue to incorporate the excised tissue in the fluid circuit;
   f. providing a photoplethysmographic device including an emitter and a photodetector;
   g. positioning the emitter so that light output by the emitter is incident on the excised tissue;
   h. positioning the photodetector so that a portion of the light output by the emitter passes through the excised tissue and is incident on the photodetector;
   i. introducing blood into the fluid circuit to be input to the pump mechanism;
   j. incorporating a sample access port in the fluid circuit for sampling the blood in the fluid circuit and for running the sampled blood through a reference instrument to obtain reference measurements;
   k. energizing the pump mechanism to move the blood through the excised tissue;
   l. energizing the emitter to output light;
   m. pairing data from the photodetector and one or more reference measurements of the obtained reference measurements; and
   n. processing the paired data to calibrate the photoplethysmographic device.

2. The method of claim 1 including the step of connecting the fluid circuit to the venous return portion of the excised tissue.

3. The method of claim 2 wherein the blood in the fluid circuit is enclosed to prevent exposure of the blood to ambient air.

4. The method of claim 1 including the step of incorporating a tonometer into the fluid circuit to set a partial pressure of one or more gases in the blood in the fluid circuit.

5. The method of claim 1 wherein the one or more reference measurements comprises reference measurements of blood analytes.

6. The method of claim 1 wherein the one or more reference measurements comprises reference measurements of hemodynamic parameters including at least one of heart rate, respiratory rate, circulating blood volume, perfusion index, and blood pressure.

* * * * *